(12) United States Patent
Bauer

(10) Patent No.: US 7,668,589 B2
(45) Date of Patent: Feb. 23, 2010

(54) INTEGRATED, PLURAL-SIGNAL, HEART-SIGNAL SENSOR SYSTEM AND RELATED DATA-PRESENTATION METHODOLOGY

(75) Inventor: Peter T. Bauer, West Linn, OR (US)

(73) Assignee: Inovise Medical, Inc., Portland, OR (US)

(\*) Notice: Subject to any disclaimer, the term of this patent is extended or adjusted under 35 U.S.C. 154(b) by 652 days.

(21) Appl. No.: 11/257,613

(22) Filed: Oct. 25, 2005

(65) Prior Publication Data

US 2006/0100535 A1 May 11, 2006

Related U.S. Application Data

(60) Provisional application No. 60/626,640, filed on Nov. 9, 2004.

(51) Int. Cl.
*A61B 5/044* (2006.01)

(52) U.S. Cl. ............... 600/513; 600/514; 600/528; 600/523

(58) Field of Classification Search .......... 600/508–528
See application file for complete search history.

(56) References Cited

U.S. PATENT DOCUMENTS

| 4,840,183 A | 6/1989 | Takahashi et al. |
| 6,527,729 B1* | 3/2003 | Turcott ...................... 600/528 |
| 7,260,429 B2* | 8/2007 | Siejko et al. ................. 600/514 |
| 2004/0220487 A1 | 11/2004 | Vyshedskiy et al. |

\* cited by examiner

*Primary Examiner*—Scott M Getzow
(74) *Attorney, Agent, or Firm*—Jon M. Dickinson, PC; Robert D. Varitz, PC

(57) ABSTRACT

A system and a related methodology for gathering, during a selected time span, and from a common anatomical site, time-contemporaneous ECG-electrical and heart-sound signals including (1) processing such signals to effect (a) time-based, related ECG fiducials, and (b) systolic and diastolic heart-sound indicators, and (2) creating a reportable data stream which communicates such effected fiducials and indicators in a manner whereby time-based relationships between them, and non-time-based differentiation between systolic and diastolic heart-sound indicators, are made visually discernible. The methodology of the invention may also be implemented strictly for the gathering and processing of heart sounds.

7 Claims, 2 Drawing Sheets

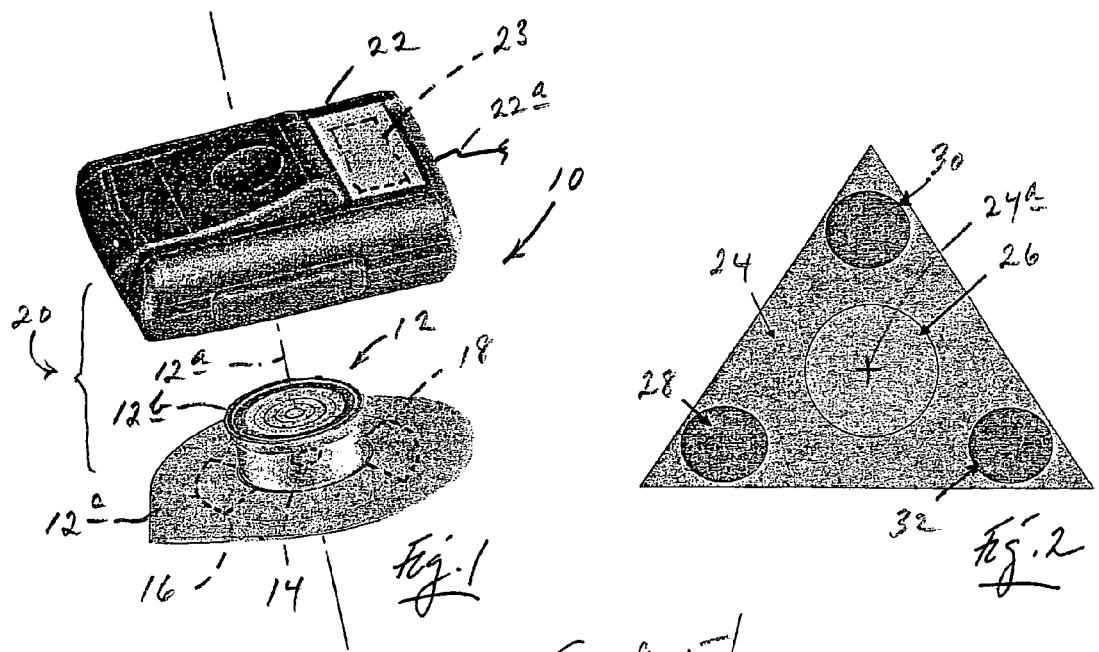
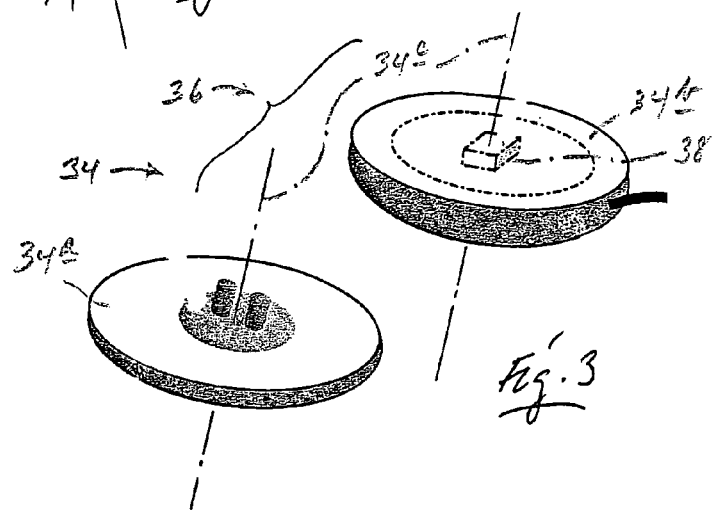
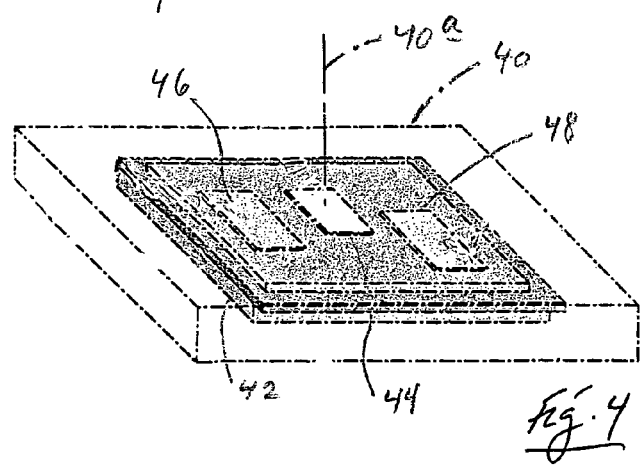

INTEGRATED, PLURAL-SIGNAL, HEART-SIGNAL SENSOR SYSTEM AND RELATED DATA-PRESENTATION METHODOLOGY

CROSS REFERENCE TO RELATED APPLICATION

This application claims filing date priority to the filing date of U.S. Provisional Patent Application Ser. No. 60/626,640, filed Nov. 9, 2004 for "Integrated, Plural-Signal, Heart-Signal Sensor and Related Methodology". The entire disclosure content of that prior filed provisional application is herby incorporated herein by reference.

BACKGROUND AND SUMMARY OF THE INVENTION

This invention proposes the structures and uses of various styles of combined electrical and acoustic sensors for variously gathering, in a related system, skin-contact anatomical ECG electrical and heart-sound data. This system is referred to herein as a patient-portable, heart-condition monitoring and reporting system. The invention also proposes a unique common-time-based graphical manner of displaying relevant, interrelated ECG and heart-sound data in a highly intuitive way for reading and understanding by medical personnel. The invention thus offers improvements in the field of heart-condition evaluation wherein there is a continuum of activity seeking to make more robust and accurate the extensively growing field of medical assessment of the healths of people's hearts. It especially enhances the utility and confidence of using carefully gathered simultaneous ECG-electrical and heart-sound-audio data in the quest for improved heart-behavior assessment.

The system proposed and offered by the invention features a sensor device and associated circuitry which is/are small, highly portable, and user-wearable (as for use in a "home heart-condition" monitoring and reporting practice). In accordance with the invention, a small, singular (or plural if desired) sensor device(s) is(are) designed to capture heart sounds from a selected region or site on the anatomy, along with plural ECG electrical signals (plurals leads) which signals are collected from closely adjacent electrically and physically spaced surface-skin regions that are symmetrically located relative to where heart sounds are gathered. Plural electrodes provided for electrical signal gathering are preferably symmetrically disposed with respect to a central "collection axis" along which a sound transducer, or transducers, (of various selectable types) in the sensor picks up heart-sound signals, such as the $S_1$, $S_2$, $S_3$ and $S_4$ heart-sound signals.

The apparatus of the invention is extremely small, and, as is suggested above, is intended to be useable as a portable home-monitoring unit if so desired, preferably with onboard signal-processing circuitry that processes gathered ECG-electrical and heart-sound-audio signals in a manner preparatory for the creation of an output data stream or signal, which is effective/constructed to create a unique and very intuitive combined-information display. This output data stream may either be coupled locally to an appropriate display device, or it may be prepared for transmission, as over the Internet, to a remote site for display and review purposes.

The display which results from the created output data stream is a highly intuitive display which includes, on a common time base, (a) a track presenting an ECG vector (terminology known in the art) which is derived directly from ECG signals to represent a person's heart electrical activities, with selected fiducials, such as the onset of the Q wave, clearly marked in relation to this vector, (b) a track which displays the directly detected heart-sound audio signals, and then, (c) on the upper and lower (positive and negative) sides of what is referred to herein as a neutral time-base axis, or line, upwardly and downwardly extending vertical graphical excursions, also referred to herein as intuitive heart-sound surrogates, which indicate the locations of the four above-identified heart sounds if and when detected. Excursions marking heart sounds which depart upwardly from the neutral axis line are those which are relatable directly to systolic heart behavior, and those which project downwardly from the neutral axis line related directly to diastolic behavior.

This very intuitive heart-sound detection display quickly enables a viewer to assess the information presented in the display with respect to the associated heart's health and condition. Additionally, heart-sound marking excursions pictured relative to the mentioned neutral axis line may take the form of rectangular, darkened, pulse-like, rectangular blocks who's heights and widths may be calibrated to describe frequency content and other characteristics of detected heart sounds. Such pulse-like blocks are also highly intuitive in nature with respect to their quick information-giving capabilities.

These and other features and advantages which are offered by the invention will become more fully apparent as the description which now follows is read in conjunction with the accompanying drawings.

DESCRIPTION OF THE DRAWINGS

FIG. 1 provides an isometric illustration of one form of compact electrical and audio sensor which includes a pair of electrically differentiated electrical-signal electrodes, and which is intended for coupling releasably to a second component in the form of a circuit-housing adapter unit (shown at the top of this figure) which is coupled appropriately for outputting a display-producing output signal (output data stream) in accordance with practice of the invention. A bracket in FIG. 1 is utilized to illustrate the inter-engageability of the two units which are shown in FIG. 1.

FIG. 2 is a simplified, bottom, plan view of yet another compact sensor which includes a central audio transducer, and three equi-angularly and symmetrically spaced, distributed ECG electrical-signal electrodes.

FIG. 3 illustrates another two-component arrangement including a wafer-like sensor which is releasably coupleable to a circuit-containing, wafer-like adapter, with the wafer-like sensor including plural ECG electrodes, and a central region which can communicate audio signals mechanically to an accelerometer-type audio transducer contained directly in the adapter unit. A bracket is also employed in this figure to express the operative interrelationship intended between the two components shown in FIG. 3.

FIG. 4 illustrates yet one more compact sensor which includes an appropriate audio transducer, plural ECG-gathering electrodes, and appropriate onboard circuitry coupled to these elements for the purpose of creating a display enabling output signal (output data stream) in accordance with practice of the invention.

DETAILED DESCRIPTION OF THE INVENTION

Figure 5:
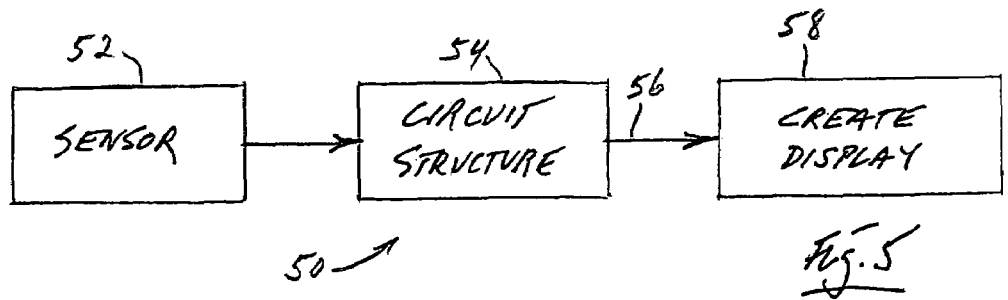
FIG. 5 is a simplified, block/schematic diagram generally illustrating the overall organization and operation of the present invention.

Turning attention now to the drawings, and beginning first of all with FIGS. 1-4, inclusive, in FIG. 1, illustrated generally at 10 is what is referred to herein, as mentioned earlier, as a patient-portable, heart-condition monitoring and reporting system which includes a small and very portable, single-site, anatomy-contact sensor 12 having a sensor axis 12a, a body 12b and a flexible flange structure 12c. An audio transducer, or audio sensing element, 14 is hidden within sensor body 12b. Also included are two electrically and physically spaced ECG-gathering electrodes, or electrical-signal sensing elements, 16, 18 which are carried on the underside of flange structure 12c. Preferably, transducer 14 sits directly on axis 12a, and electrodes 16, 18 are symmetrically spaced and disposed relative both to transducer 14 and to axis 12a. It is the underside of sensor 12 in FIG. 1 which is placed against a selected anatomical site during use of the system of this invention to gather skin-contact ECG-electrical and heart-sound-audio signals generally centered on axis 12a. Sensing elements 14, 16, 18 are referred to collectively herein as plural-parameter sensing elements.

Disconnectively coupleable, as suggested by a bracket 20 in FIG. 1, is an adapter unit 22 which can be coupled and decoupled operatively with respect to sensor 12, with adapter 22 including within it circuit structure 23 which is referred to herein as reporting, signal-processing circuit structure.

In accordance with practice of the invention, when the structure shown in FIG. 1 is operating with respect to a particular person, information gathered by sensing elements 14, 16, 18 is processed by circuit structure 23 to produce what is referred to herein as an output signal information-reporting stream. This output stream is fed outwardly to appropriate reception and display-presentation apparatus via wiring in a cable shown at 22a in FIG. 1. If desired, of course, a wireless feed of such output information could be implemented utilizing conventional techniques.

Figure 8:
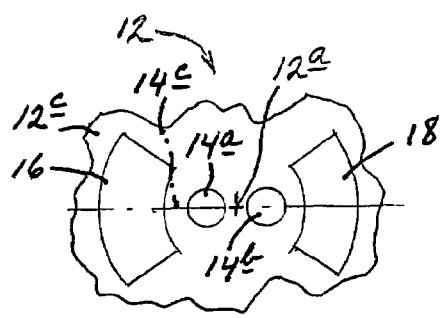
FIG. 8 is a fragmentary view illustrating, in the context of just one of the several sensors pictured in FIGS. 1-4, inclusive, and in particular in the context of the sensor of FIG. 1, a plural (dual) sound-transducer arrangement constructed in accordance with the invention.

Digressing for a moment to FIG. 8 which is related to FIG. 1, here sensor 12, in a somewhat modified form, is shown including a pair of side-by-side audio transducers 14a, 14b which lie substantially equidistant from sensor axis 12a on a line 14c which intersects axis 12a, and bisects electrodes 16, 18. This kind of a plural-audio-transducer arrangement may be useful, for example, in enabling selection of the "best" available sound signal, and/or in enabling noise suppression of unwanted, and potentially interfering ambient sounds.

Those skilled in the relevant art will recognize that such a plural-sound-transducer organization may be employed in any and all of the other three sensor structures still to be described herein.

FIG. 2 illustrates the bottom, skin-contacting side of another form of a small and portable sensor 24. This sensor, which possesses a sensing axis 24a, includes, as sensing elements, a central audio transducer 26 which is substantially centered on a sensing axis 24a, and three, equi-angularly and symmetrically distributed electrical signal electrodes 28, 30, 32 in FIG. 2.

The side of sensor 24 which faces the viewer in FIG. 2 is the skin-contacting side of this sensor.

In FIG. 3, here there is illustrated yet another small and portable sensor 34 which is employable in the practice of this invention. Sensor 34 includes a pair of releasably coupleable, wafer-like sensor units 34a, 34b. A bracket 36 in FIG. 3 is provided to illustrate the fact that units 34a, 34b, when coupled, co-act with one another along a sensor axis shown at 34c.

Unit 34a in sensor 34, whose underside in FIG. 3 provides the skin-contact side of sensor 34, carries on its underside (though not directly shown herein), a plurality of electrically and spatially independent electrodes which are distributed symmetrically with respect to axis 34c.

Within the body of unit 34b there is provided an acoustic transducer 38 which acts along axis 34c to collect heart-sound signals. In the case of sensor 34, acoustic signals are communicated to transducer 38 centrally and mechanically through the body of unit 34a.

Focusing attention now on FIG. 4, here shown is another small and portable sensor 40 which is usable in the practice of the present invention. Associated with sensor 40 is a signal collection axis 40a, and included within the body of sensor 40 are (a) plural perimeter electrodes, such as electrode 42, (b) an audio transducer 44, (c) a memory chip 46 which may be employed to gather and store collected information, and (d) circuit structure 48 which processes signals gathered by the electrodes and the transducer for outward transmission to external equipment in the form of an output signal information-reporting stream.

In the cases of all of the specific sensors illustrated herein, it is preferable, and it has been mentioned with respect to two of the illustrated sensors, that the signal-processing circuitry be included in some fashion within the body of the associated sensor.

Turning attention now to FIG. 5, the overall system and methodology of the invention are shown generally at 50, with a block 52 in FIG. 5 representing the sensor structure which gathers ECG and audio information, and a block 54 representing circuit structure employed to process gathered signals, and to create, on an output line 56, an output signal information-reporting stream which is supplied to a block 58, wherein, from the construction of the output signal on line 56, a graphical output display is created in accordance with practice of the invention. This output data stream, with respect to EGG information, is said herein to include, inter alia, EGG vector information from which certain EGG fiducials, shortly to be described, are produced.

Figure 6:
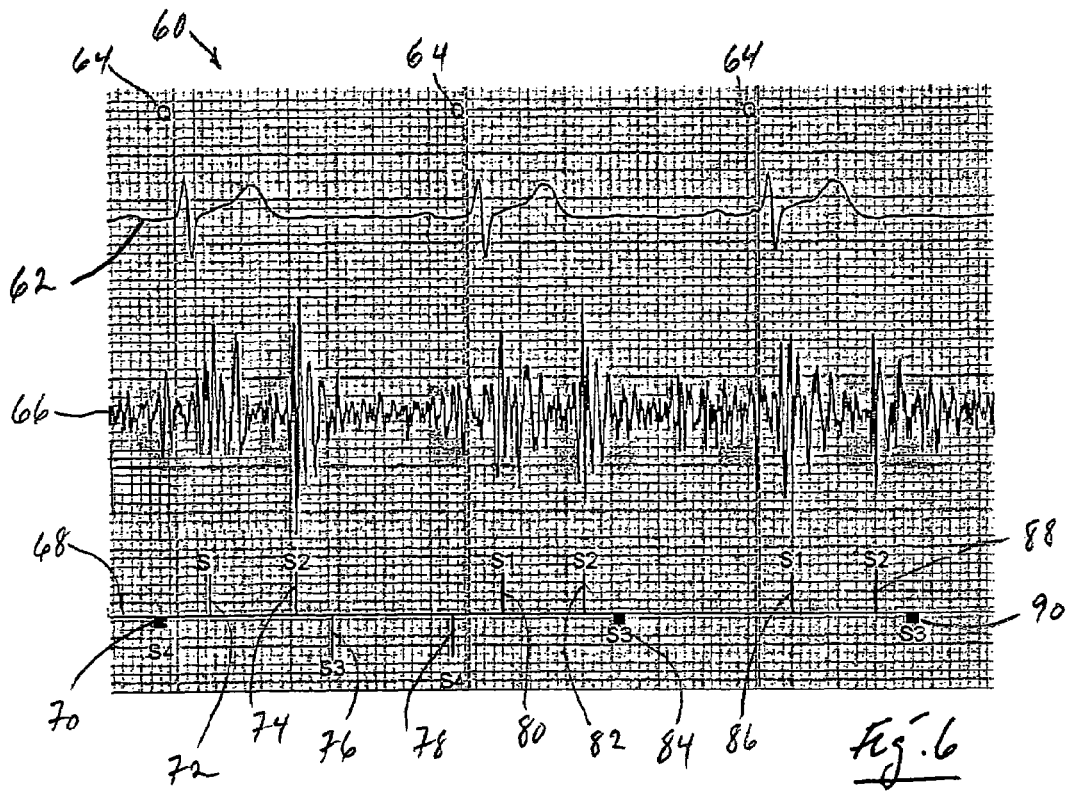
FIG. 6 is a representative graphic display which has been prepared in accordance with the content of an output signal data stream produced during practice of the invention.

FIG. 6 illustrates such a display generally at 60. As can be seen, this display includes (a) an ECG, time-varying waveform 62, above which are indicated Q-onset fiducials 64, also referred to as selected, keyed-to EGG fiducials, (b) an actual audio, or acoustic, time-varying waveform 66 derived from a gathered audio signal, and (c) a horizontal, neutral axis line 68 above and below which are shown upwardly and downwardly extending, non-time-varying graphical lines and rectangular blocks (marks, or markers) that constitute time-positioned "departures" from this neutral axis 70, 72, 74, 76, 78, 80, 82, 84, 86, 88 and 90. These "departures" above and below line 68, also referred to herein as audio event presentations which are datumed to that line, represent heart-sound information presented in what is referred to herein as a "laddergram" display, or manner, with those departures which extend above line 68 are associated herein to systolically-related heart activity, and those which extend below line 68 are associated herein with diastolically-related heart activity. As will be observed, the use of these departure markers above and below a neutral axis line offer a viewer very intuitive understanding of the nature of a person's heart condition when these markers are examined in the presence of waveforms 62, 66, and fiducials 64. The "systolic-up, diastolic-down" pattern of presentation is, of course, reversible if desired. For convenience, the "up direction is referred to herein as a positive direction and the "down" direction as a negative direction.

Figure 7:
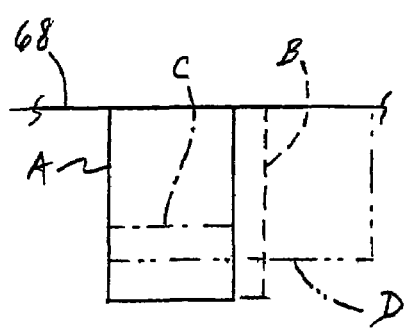
FIG. 7 is a fragmentary, schematic detail illustrating how certain rectangular blocks in a display, such as in the display of FIG. 6, may offer information in accordance with their specific width and height characteristics.

Markers 70, 84 and 90 are, as can be seen, specifically rectangular and block-like in nature, and according to the invention, their widths and/or heights may be designed to illustrate other heart-sound characteristics, such as strength, frequency content, and other things. Exactly what these height and width characteristics relate to is purely a matter of user choice. In this regard, FIG. 7 schematically illustrates the concept that rectangular markers, such as markers 70, 84, 90, may have various different height and width aspect ratios. Four of these ratios are indicated at A, B, C, D in FIG. 7. It will be apparent that where, for example, these height and width characteristics are linked to certain heart-sound features, aspect ratio can become an immediate, intuitive indicator of heart condition.

Thus a preferred embodiment, and a preferred practice methodology, associated with this invention have been illustrated and described. The end result of signal gathering practiced in accordance with the invention is a display such as that pictured in FIG. 6 which offers highly intuitive information relating to the condition of a person's heart.

In a broad manner of speaking, the methodology of this invention can be characterized as a practice involving the steps of: (a) during a selected time span, gathering, from a common anatomical site, time-contemporaneous ECG-electrical and heart-sound-audio signals; (b) processing such signals to effect (1) time-based, related ECG fiducials, and (2) systolic and diastolic heart-sound indicators; and (c) creating a reportable data stream which communicates such effected fiducials and indicators in a manner whereby time-based relationships between them, and non-time-based differentiation between systolic and diastolic heart-sound indicators, are made visually discernable in an intuitive way.

Accordingly, while a preferred embodiment and manner of practicing the invention have been described herein, with several different useable types of sensors illustrated, it is appreciated that variations and modifications may be made without departing fro the spirit of the invention.

I claim:

1. A patient-portable heart-condition monitoring and reporting system comprising
    an anatomy-contact sensor including an audio sensing element, and plural electrical-signal sensing elements, and
    signal-processing circuit structure operatively connected to said elements, operable, during a selected time interval, (a) to collect therefrom audio and electrical-ECG signals detected by said elements under a circumstance with said sensor contacting a selected anatomical site on a person's anatomy, and (b) to create therefrom an output signal constructed to generate, on a common time scale, a time-based graphical, laddergram display keyed to selected ECG fiducials, and including time-specific audio-event heart-sound marks datumed to, and projecting linearly from opposite, upper and lower sides of, a generally horizontal neutral axis, said marks including both systolically-related heart-sound marks deployed on one of said opposite sides of said axis, and diastolically-related heart-sound marks deployed on the other, opposite side of said axis.

2. The system of claim 1, wherein said systolically-related and diastolically-related marks are characterized with excursion heights measured relative to said axis which are indicators of the intensities of the respective, associated heart sounds.

3. The system of claim 2, wherein said output signal is further constructed to generate, in said display, certain heart-sound marks having lateral widths whose sizes are related to frequency and/or intensity-content characteristics of the respective, associated heart sounds.

4. The system of claim 1, wherein said output signal is further constructed to generate, in said display, certain heart-sound marks having lateral widths whose sizes are related to frequency and/or intensity-content characteristics of the respective, associated heart sounds.

5. The system of claim 1, wherein said output signal is further constructed to generate additional heart-sound information in the forms of ECG and heart-sound-acoustic waveforms that are time aligned with said laddergram-display marks.

6. During a selected time span, gathering time-contemporaneous ECG-electrical and heart-sound-acoustic signals,
    processing such electrical and acoustic signals to create a display-effecting output signal, and
    employing the created output signal, producing therefrom a time-based laddergram display (a) designed for reading in synchronized relation with at least one of an ECG waveform marked with selected fiducials, and an audio waveform picturing heart acoustic activity, and (b) possessing time-specific, audio-event, heart-sound marks datumed to, and projecting linearly from opposite, upper and lower sides of, a generally horizontal, neutral axis, such marks including both systolically-related marks deployed on one of the opposite axis sides, and diastolically-related marks deployed on the other axis side.

7. During a selected time span, gathering time-contemporaneous ECG-electrical and heart-sound-acoustic signals,
    processing such electrical and acoustic signals to create a display-effecting output signal, and
    employing the created output signal, producing therefrom a time-synchronized, common-time-based display which includes (a) an ECG waveform marked with selected fiducials, (b) an audio waveform picturing heart acoustic activity, and (c) a laddergram possessing time-specific, audio-event, heart-sound marks keyed to the selected fiducials, and datumed to, and projecting linearly from opposite, upper and lower sides of, a generally horizontal, neutral axis, such marks including both systolically-related marks deployed on one of the opposite axis sides, and diastolically-related marks deployed on the other axis side.

* * * * *